United States Patent
Boese et al.

(10) Patent No.: US 7,899,152 B2
(45) Date of Patent: Mar. 1, 2011

(54) METHOD FOR THE THREE-DIMENSIONAL REPRESENTATION OF A MOVING STRUCTURE BY A TOMOGRAPHIC METHOD

(75) Inventors: Jan Boese, Eckental (DE); Wolfgang Härer, Erlangen (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 229 days.

(21) Appl. No.: 12/221,938

(22) Filed: Aug. 7, 2008

(65) Prior Publication Data

US 2009/0092225 A1 Apr. 9, 2009

(30) Foreign Application Priority Data

Aug. 10, 2007 (DE) .......................... 10 2007 037 996

(51) Int. Cl.
*A61B 6/00* (2006.01)
(52) U.S. Cl. .................... 378/19; 378/8; 378/21; 378/22
(58) Field of Classification Search .................. 378/4, 8, 378/19
See application file for complete search history.

(56) References Cited

U.S. PATENT DOCUMENTS

| 5,396,418 | A  | * | 3/1995  | Heuscher ........................ 378/15 |
| 6,512,807 | B1 | * | 1/2003  | Pohlman et al. .................. 378/4  |
| 6,888,914 | B2 | * | 5/2005  | Edic ................................ 378/4 |
| 6,904,121 | B2 | * | 6/2005  | Claus et al. ..................... 378/21 |
| 7,245,698 | B2 |   | 7/2007  | Pang et al. |
| 7,738,626 | B2 | * | 6/2010  | Weese et al. .................... 378/41 |
| 2001/0005410 | A1 |   | 6/2001 | Rasche et al. |
| 2002/0141532 | A1 | * | 10/2002 | Koppe et al. ................... 378/21 |
| 2003/0040669 | A1 | * | 2/2003 | Grass et al. .................... 600/407 |
| 2004/0264634 | A1 | * | 12/2004 | Claus et al. ..................... 378/21 |
| 2004/0264635 | A1 | * | 12/2004 | Eberhard et al. ............... 378/22 |
| 2004/0264636 | A1 | * | 12/2004 | Claus et al. ..................... 378/26 |
| 2005/0105679 | A1 | * | 5/2005 | Wu et al. ........................ 378/22 |
| 2005/0251010 | A1 |   | 11/2005 | Mistretta et al. |
| 2006/0120507 | A1 |   | 6/2006 | Brunner et al. |

FOREIGN PATENT DOCUMENTS

DE 199 58 864 A1 6/2001

OTHER PUBLICATIONS

Liu et al., Generalized Tomosynthesis for Focusing on an Arbitrary Surface, IEEE Transactions on Medical Imaging, vol. 8, Nol. 2, Jun. 1989, pp. 168-172.*

(Continued)

*Primary Examiner* — Edward J Glick
*Assistant Examiner* — Alexander H Taningco

(57) ABSTRACT

The invention relates to a method for a three-dimensional representation of a moving structure by a tomographic method, in which during one recording pass a series of projection recordings is registered by an imaging unit at different recording angles between a start position and an end position, it being possible to reconstruct three-dimensional image data from the projection recordings with the following steps: a) generation of tomosynthesis projection recordings along a tomosynthesis scanning path; b) interpolation of the data of the tomosynthesis projection recordings in accordance with an interpolation algorithm in order to generate a projection data set; c) use of a tomosynthesis reconstruction method on the projection data set in order to generate a tomosynthesis volume image; d) repetition of steps b) and c) for all times of interest, and e) display of tomosynthesis representations from the tomosynthesis volume images.

18 Claims, 6 Drawing Sheets

OTHER PUBLICATIONS

M. Zellerhoff, B. Scholz, E.-P. Rührnschopf, T. Brunner, "Low contrast 3D-reconstruction from C-arm data", Medical Imaging 2005: Physics of Medical Imaging, Proceedings of SPIE vol. 5745, pp. 646-655.

Günter Lauritsch, Jan Boese, Lars Wigström, Herbert Kemeth and Rebecca Fahrig, "Towards Cardiac C-Arm Computed Tomography", IEEE Trans. Med. Imaging 25(7): pp. 922-934 (2006).

Günter Lauritsch and Wolfgang H. Härer, "A theoretical framework for filtered back-projection in tomosynthesis". In: Hanson K M (Hrsg) Medical Imaging 1998: Image Processing vol. 3338. SPIE, Bellingham (USA), pp. 1127-1137.

C. Badea, Z. Kollitsi ,N. Pallikarakis, "Image quality in Extended arc Filtered Digital Tomosynthesis", Acta Radiologica, vol. 42, issue 2 (2001); pp. 244-249.

* cited by examiner

METHOD FOR THE THREE-DIMENSIONAL REPRESENTATION OF A MOVING STRUCTURE BY A TOMOGRAPHIC METHOD

CROSS REFERENCE TO RELATED APPLICATIONS

This application claims priority of German application No. 10 2007 037 996.1 filed Aug. 10, 2007, which is incorporated by reference herein in its entirety.

FIELD OF THE INVENTION

The invention relates to a method for the three-dimensional representation of a moving structure by a tomographic method.

BACKGROUND OF THE INVENTION

In medicine a frequent problem is to generate time-resolved, three-dimensional images of dynamic (time-dependent) events within objects which vary with time, from recordings of projections of the objects taken from different directions. The object to be imaged can be the human body, for example. Here, in particular, the spread of contrast agents in vessels, for example dynamic angiography, in tissue, for example perfusion, the spontaneous movement of organs, for example the heartbeat, breathing, peristalsis or swallowing, or external mechanical compression of tissue (elastography), can be considered as dynamic events. The recordings can be made with X-ray apparatus with a flat detector, as described for example in US 2006/0120507 A1.

Such a known X-ray diagnostic apparatus is illustrated in FIG. 1. As an imaging unit the X-ray diagnostic apparatus has a C-arm 2 supported in a rotatable manner on a stand 1, an X-ray source, for example an X-ray emitter 3 and an X-ray image detector 4, these being mounted on the ends of said C-arm.

The X-ray image detector 4 can be a rectangular or square flat semiconductor detector that is preferably made from amorphous silicon (aSi).

A patient support table 5 for imaging the heart of a patient to be examined, for example, is located in the beam path of the X-ray source 3. An imaging system 6 which receives the image signals from the X-ray image detector 4 and generates a three-dimensional reconstruction of the object to be mapped, is connected to the X-ray diagnostic apparatus. The imaging results can then be viewed on a monitor 7.

Until now, computed tomography (CT) has been employed for time-resolved three-dimensional images of dynamic events. It permits—firstly for static objects—a more or less exact three-dimensional reconstruction of the internal parts of the body, since it records projections of the object to be imaged from virtually all directions; typically from a circular orbit of the tube and detector around the patient, as described in Zellerhoff et al. [1]. For dynamically moving objects, periodically repeated CT scans are mostly used, as in Lauritsch et al. [2], in order to record the object to be imaged at different time intervals. The achievable time resolution is then determined by the time required for an individual CT scan and in many cases is inadequate for rapid movements, for example the heart or the flow of a contrast agent. Cardiac imaging and also perfusion imaging are available with CT. Perfusion imaging with CT is generally limited to a relatively thin layer. Time-related high-resolution cardiac imaging is also possible with ultrasonic devices. The elastographic method is also technically feasible in the field of ultrasonic imaging.

SUMMARY OF THE INVENTION

The invention is based on the object of developing a method in such a way that functional imaging with C-arm angiographic systems can be easily realized in the interventional environment.

The method relates to the three-dimensional representation of a moving structure by means of a tomographic method, in which during one recording pass a series of projection recordings is registered by an imaging unit at different recording angles between a start position and an end position, it being possible to reconstruct three-dimensional image data from the projection recordings. This type of three-dimensional X-ray imaging of dynamic events can be implemented by means of flexible C-arm X-ray apparatus.

The object is achieved according to the invention by means of the following steps:
a) Generation of tomosynthesis projection recordings along a tomosynthesis scanning path,
b) Interpolation of the data of the tomosynthesis projection recordings in accordance with an interpolation algorithm in order to generate a projection data set,
c) Use of a tomosynthesis reconstruction method on the projection data set in order to generate a tomosynthesis volume image,
d) Repetition of steps b) and c) for all times of interest, and
e) Display of tomosynthesis representations from the tomosynthesis volume images.

A scanning path or curve is a specific type of movement of the measuring system, consisting of an X-ray tube and an X-ray image detector, around the patient. Critical to the scanning is the movement of the X-ray focus, which is described in the following. The X-ray image detector can be made to track the movement of the focus, but does not have to; it can even stop. It is only necessary to ensure that it receives as often as possible the radiation that has passed through the area of the patient that is of interest, for example the heart. In principle, a distinction is made in the following between closed scanning curves—which always run in the same direction—and non-closed scanning curves—which run in opposite directions to one another. In this case closed scanning curves deliver a more useful type of scanning and, due to the smoothness of the mechanical movement, can usually be more easily realized and more rapidly traversed.

Advantageously, closed tomosynthesis scanning paths can have a circular, elliptical, loop or spiral shape.

Alternatively, the tomosynthesis scanning path can be non-closed, it being possible according to the invention for it to have a spiral or linear shape and to run in both directions.

In order to further improve the time resolution, in addition to faster measurement with tomosynthesis methods, projection images are determined at fixed times $t_0$ and reconstructed from the measured data with the aid of a suitable time interpolation.

It has proved to be advantageous if the interpolation algorithm contains a linear interpolation, a polynomial interpolation or a spline interpolation. Other interpolation methods, such as the "nearest neighbor" interpolation, for example, are likewise possible according to the invention.

According to the invention, the tomosynthesis reconstruction method can be a back-projection method or an algebraic method.

In an advantageous fashion, the display of the tomosynthesis representations can include animated representations such as dynamic angiographical recordings and/or graphical representations of functional parameters, which can be derivations of functional parameters and graphical representations of the "cerebral blood flow", "cerebral blood volume" and/or "time-to-peak".

The derivation of functional parameters is calculated from the measured sequences of 3D-images, that is to say for each pixel an individual parameter is determined from a sequence of timed samples in order to make representation and interpretation easier. The exact mathematical implementation is sufficiently well known for the above-mentioned common, exemplary parameters. In the present case the term derivation should not be interpreted in the strictly mathematical sense. The derived functional parameters are individual numerical values for each pixel, which in the customary manner can be represented in the form of gray-scale or color values.

It has proved advantageous if the method includes the following steps:
S1 Start an injection of contrast agent at a first time $t_i$,
S2 Wait for a delay time $\Delta t$,
S3 Generate a periodic tomosynthesis projection recording,
S4 Interpolate tomosynthesis projection recordings at fixed times $t_n$ from the measured data,
S5 Reconstruct three-dimensional volume images at times $t_n$ and
S6 Process and display the data for the user by:
S7a Derive functional parameters and graphical display and/or
S7b graphical display of moving images.

Furthermore, the object is achieved according to the invention in that in order to generate the projection recordings, tomosynthesis projection recordings are made at different recording angles along a tomosynthesis scanning path and that three-dimensional image data are reconstructed from the tomosynthesis projection recordings. In order to improve the time resolution and for faster measurement, tomosynthesis methods are used instead of the usual C-arm tomography in which the C-arm is rotated around the object under examination.

BRIEF DESCRIPTION OF THE DRAWINGS

The invention is explained in further detail with the aid of the exemplary embodiments illustrated in the drawing, in which.

DETAILED DESCRIPTION OF THE INVENTION

Exemplary scanning geometries for circular and linear tomosynthesis, for closed and non-closed scanning paths, are now explained in further detail with the aid of the following figures.

Figure 1:
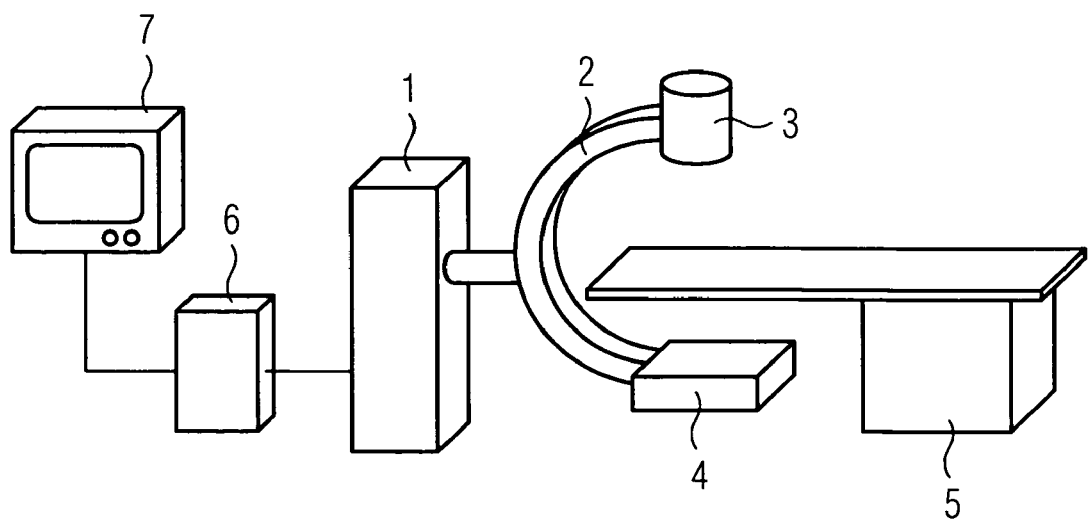
FIG. 1 shows a schematic view of a C-arm system for carrying out the method according to the invention.
Figure 2:
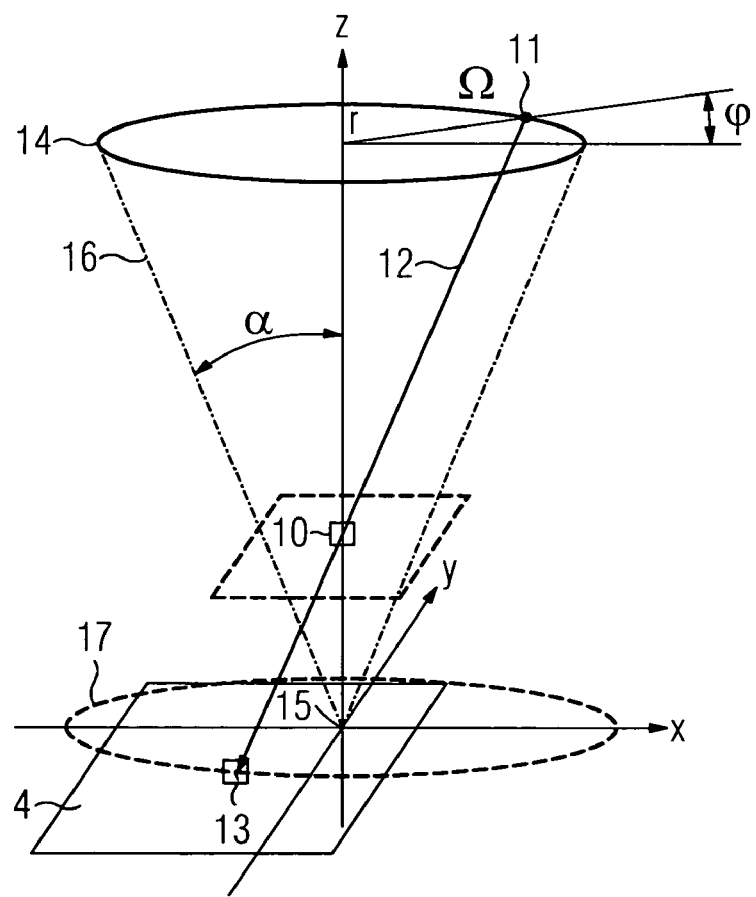
FIG. 2 shows scanning geometries for circular tomosynthesis of a closed scanning path.

A closed scanning path in which a patient—shown schematically by a voxel 10—lying on the patient support table 5, is penetrated by an X-ray beam 12 being emitted from a focus 11 of the X-ray source 3, is reproduced in FIG. 2. The X-ray beam 12 then strikes a pixel 13 of the X-ray image detector 4. The focus 11 moves around a circular tomosynthesis scanning path 14 having a radius r, whose mid-point is the Z-axis of a coordinate system 15. The tomosynthesis scanning path 14 appears as an ellipse only in the perspective representation. The side line of the cone 16 directed from the circular tomosynthesis scanning path 14 towards the origin of the coordinate system 15 makes an angle $\alpha$ to the Z-axis. The position of the focus 11 in relation to the X-axis of the coordinate system 15 is denoted by the angle $\phi$ and the spatial position by the solid angle $\Omega$. In the X/Y plane the X-ray beam 12 covers a circular path 17, around which the X-ray image detector 4 is preferably likewise displaced, so that the X-ray beam 12 always strikes the same pixel 13. This ensures that not only the central X-ray beam 12 passing through the voxel 10, but all the X-ray beams penetrating the patient always fall on the X-ray detector 4. The start point $s_{begin}$ and the end point $s_{end}$ of the closed scanning path can be identical if the scanning paths are completely traversed.

Figure 3:
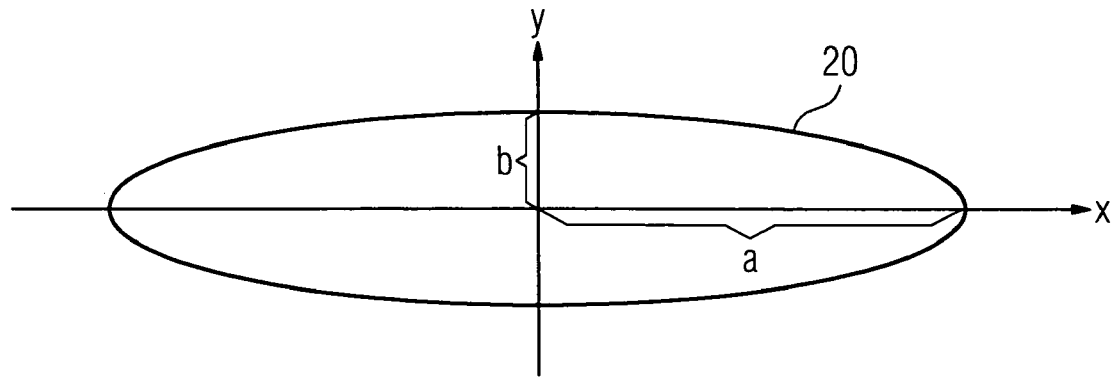
FIGS. 3 to 7 show further closed scanning paths.

A further closed scanning path seen as an ellipse 20, which has a major half-axis a and a minor half-axis b, is illustrated in a plan view in FIG. 3.

Figure 4:
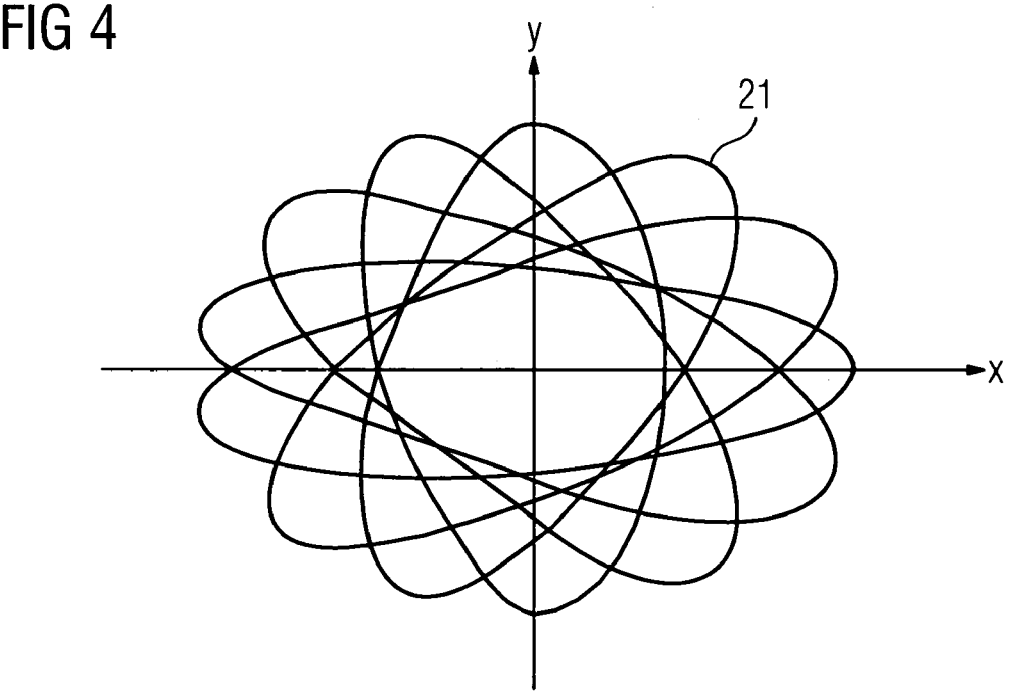

Alternatively, as shown in FIG. 4, an elliptical scan with a curve 21 can be achieved with additional rotation of the major half-axis a and cyclic rotation.

Figure 5:
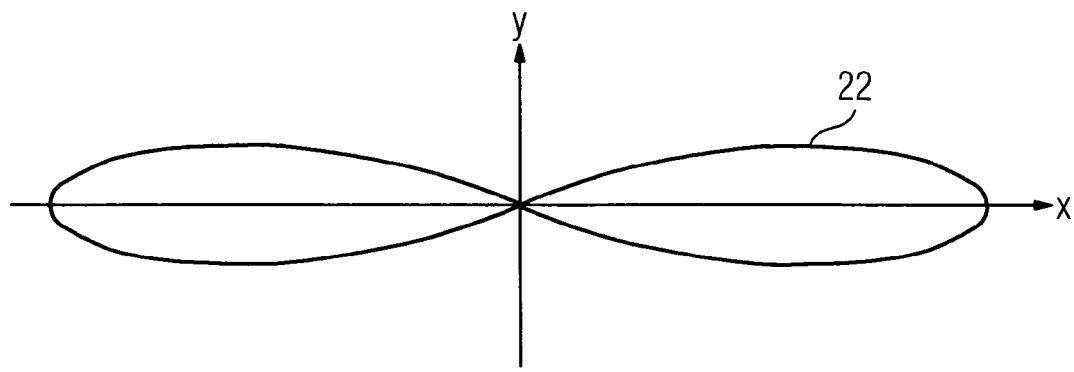

Likewise, a closed scanning curve forms a looped scan, as illustrated in the plan view of FIG. 5, in which a loop 22 is traversed as the tomosynthesis scanning path, instead of the circle 14 of FIG. 2. Alternatively, the loop-shaped scan can consist not only of two but any number of branches. In addition, the loop axis can also be rotated, thus resulting in the interlaced curve shape 23 illustrated in FIG. 6.

Figure 7A:
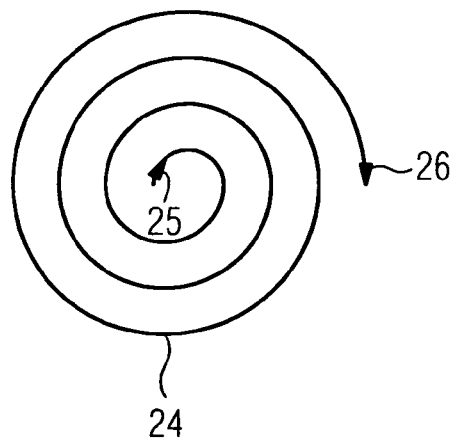
Figure 7B:
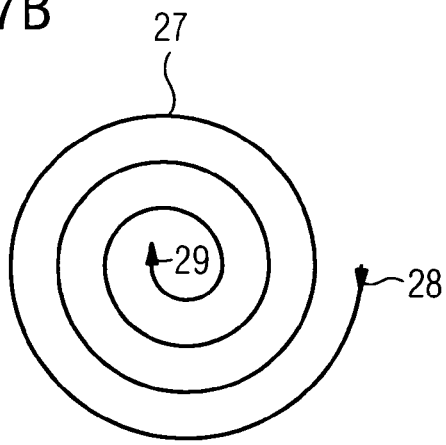

A spiral scan is shown in plan view in FIG. 7, in which on completion of a spiral 24 running outwards in a clockwise direction as shown in FIG. 7A, the direction of the deflection and not the direction of rotation is reversed, as shown in FIG. 7B. Starting from the start point 25, the focus 11 rotates outwards until it reaches the end point 26. This end point 26 corresponds to the start point 28 of a spiral 27 directed inwards and running in a clockwise direction, on which the focus reaches the end point 29 of the inwardly-directed spiral 27. This end point 29 can again be the start point 25 of the outwardly-directed spiral, that is to say a continuous movement is achieved on the closed scanning curve, so that after reaching the maximum deflection the movement is continued in the same direction of rotation but directed inwards. Correspondingly, on reaching the minimum deflection, the movement continues in the same direction of rotation but directed outwards, and so on.

Figure 8:
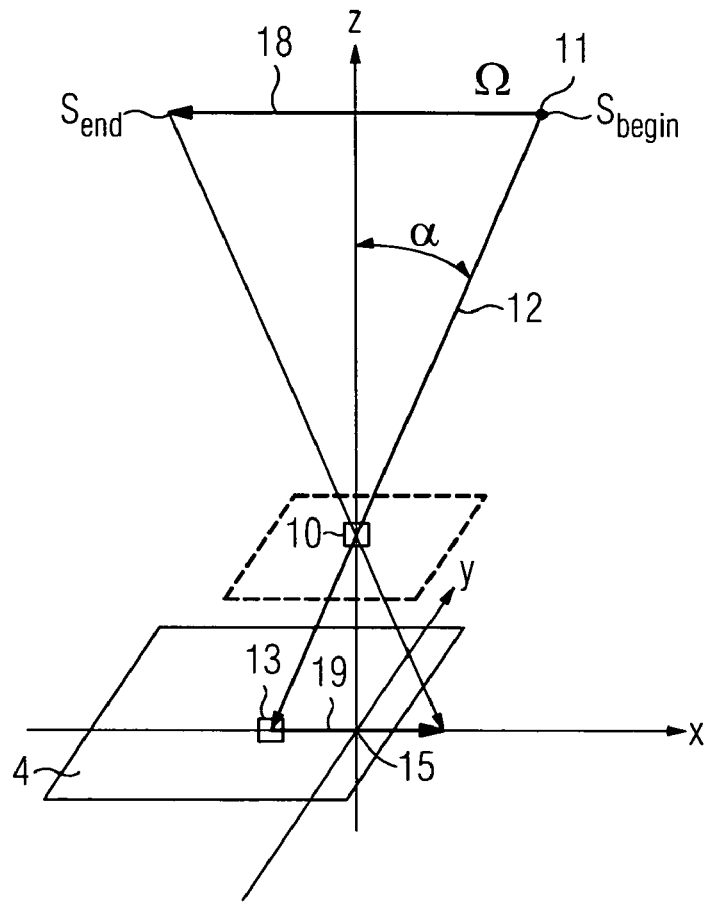
FIG. 8 shows scanning geometries for linear tomosynthesis of a non-closed scanning path.

An example of a non-closed scanning path, a linear scanning path, is now shown in FIG. 8. This means that the focus 11 moves to and fro on a linear tomosynthesis path 18, as shown by the straight arrow, the center of which lies on the Z-axis of the coordinate system 15. The end points of the linear tomosynthesis scanning path 18, the start point $s_{begin}$ and the end point $s_{end}$, form an angle $\alpha$ with the Z-axis. The solid angle $\Omega$ thus has an angle between $\alpha$ and $\alpha$. At the start position $s_{begin}$ the X-ray 12 strikes the pixel 13, which along with the X-ray image detector 4, is displaced in the direction of the X-axis in accordance with the travel of the X-ray beam 12 as indicated by the arrow 19. In so doing, the observed X-ray beam 12 always passes through the middle of the patient, the voxel 10.

Figure 9A:
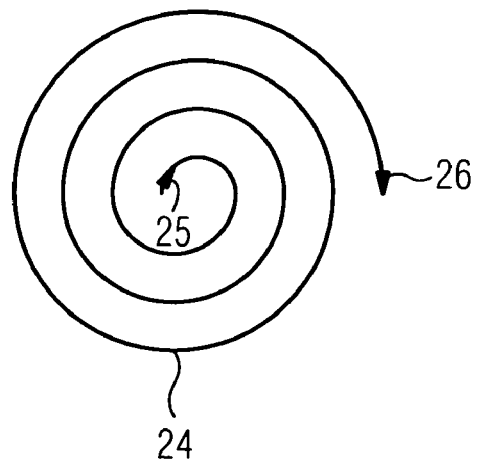
FIG. 9 shows further non-closed scanning paths.
Figure 9B:
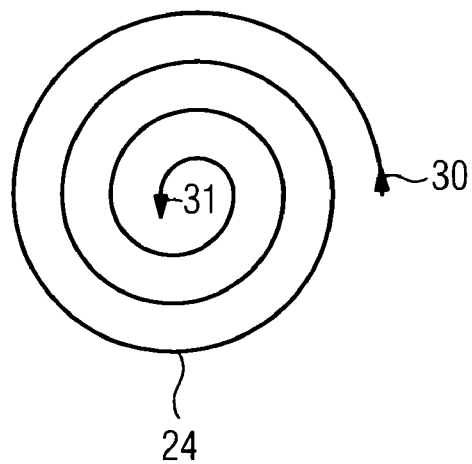

Other non-closed scanning paths can have a spiral construction, it being possible for the scanning direction to be reversed on completion of the spiral, an example of which is shown in the plan view of FIGS. 9A and 9B.

Starting from the start point 25, the focus 11 is moved on the outwardly-directed spiral 24 running in a clockwise direction 24, until it reaches the end point 26. This end point 26 corresponds to the start point 30 of the same spiral 24, which is now traversed by the focus 11 in the counterclockwise direction up to the end point 31. This end point 31 can again be the start point 25 of the outwardly-directed spiral 24, that is to say the focus 11 always moves along the same spiral path, only in the reverse direction. Non-closed scanning paths can also include a partial rotation of a closed path, for example a CT partial rotation.

Figure 10:
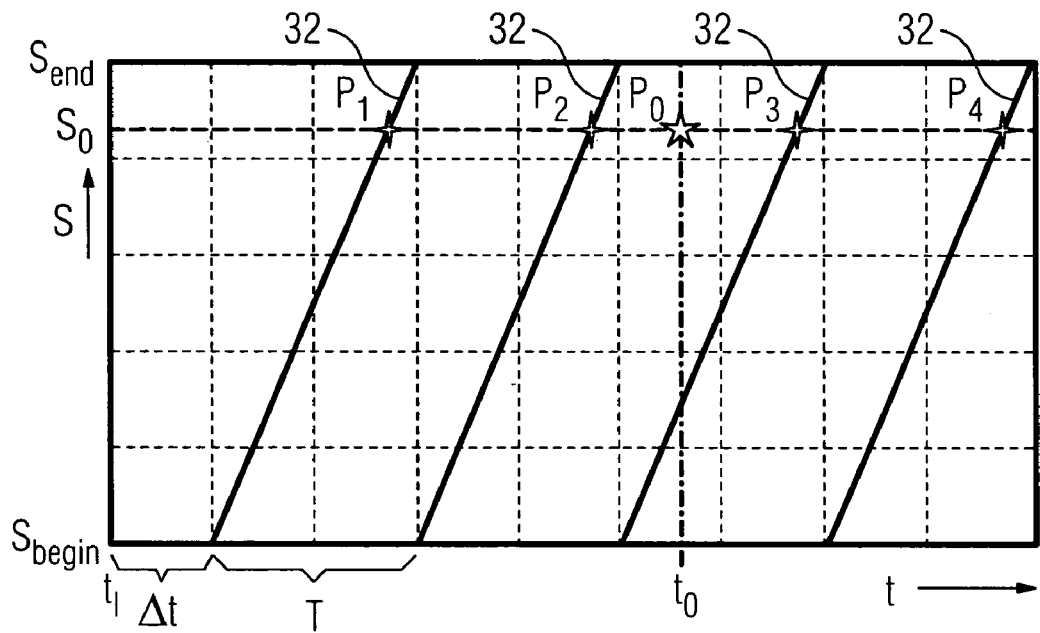
FIG. 10 shows a schematic representation of the projection recordings for a closed path curve according to FIG. 2.
Figure 11:
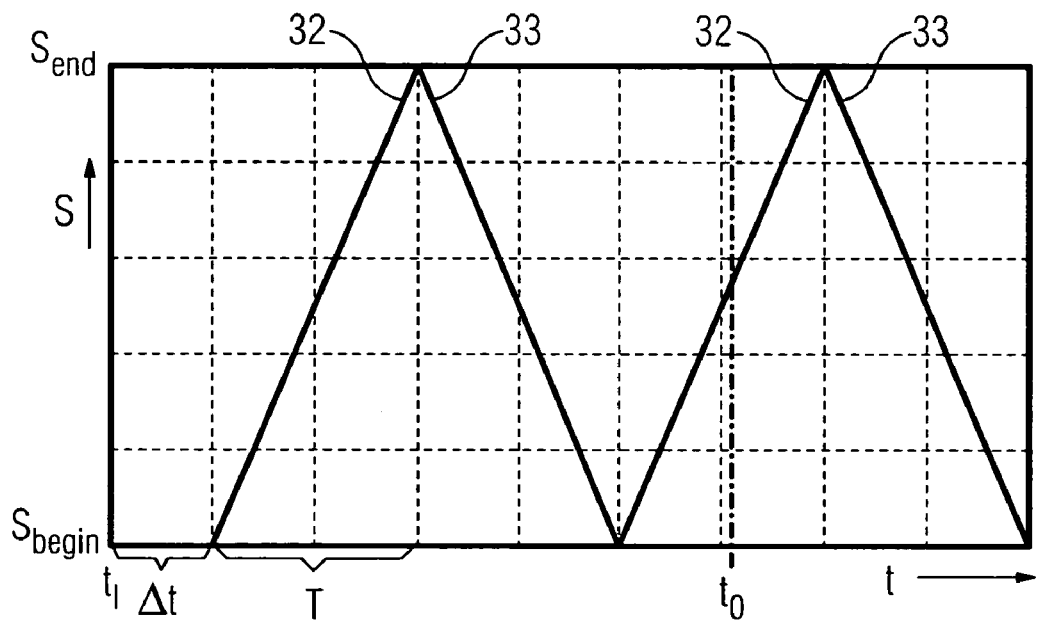
FIG. 11 shows a schematic representation of the projection recordings for a non-closed path curve according to FIG. 8.

FIGS. 10 and 11 show schematically how and at which points data is measured in relation to the path parameter s and the time t. The objective is to reconstruct volume images V(t) from the obtained projections P(s,t) at specific times in the acquisition time range. In order to obtain the most exact reconstruction possible of a volume at the time $t_0$, a projection data set P(s, $t_0$, is required at this time $t_0$, it being possible for s to include the range between $s_{begin}$ and $s_{end}$ or a partial range. However, the individual projections P(s,t) of the measured rotational recordings always occur at different times t, as is apparent from FIGS. 10 and 11. According to the invention, a searched-for projection P($s_0$, $t_0$) at the time $t_0$ is determined by a suitable interpolation along the line s=$s_0$ in FIG. 10. FIG. 10 shows the path parameters s over the recording time t for a closed path curve with a run time T, which form ascending straight lines 32, it being possible for the end point $s_{end}$ of the first straight line 32 to form the start point $s_{begin}$ of the next straight line 32. As an example, the interpolation points $P_1, \ldots, P_4$ available for $P_0$=P($s_0$, $t_0$) are illustrated in FIG. 2. This procedure has to be implemented for all values from the range of s under consideration. The projection data set P(s,$t_0$) determined in this manner can then be reconstructed by means of a suitable reconstruction method, as described in Lauritsch et al. [4] for example, in order to obtain a volume image V($t_0$) at the time $t_0$. This method as described there then has to be implemented for all times t of interest. The total time series of volume images V(t) thus obtained can only be displayed either as animation or used as the starting point for determining functional parameters.

The schematic arrangement of projection images relating to the path parameter s and the recording time t for a non-closed path curve is shown in FIG. 11. Here the direction of movement is reversed at the points $s_{begin}$ and $s_{end}$, so that the ascending straight lines 32 change to the descending straight lines 33.

Figure 12:
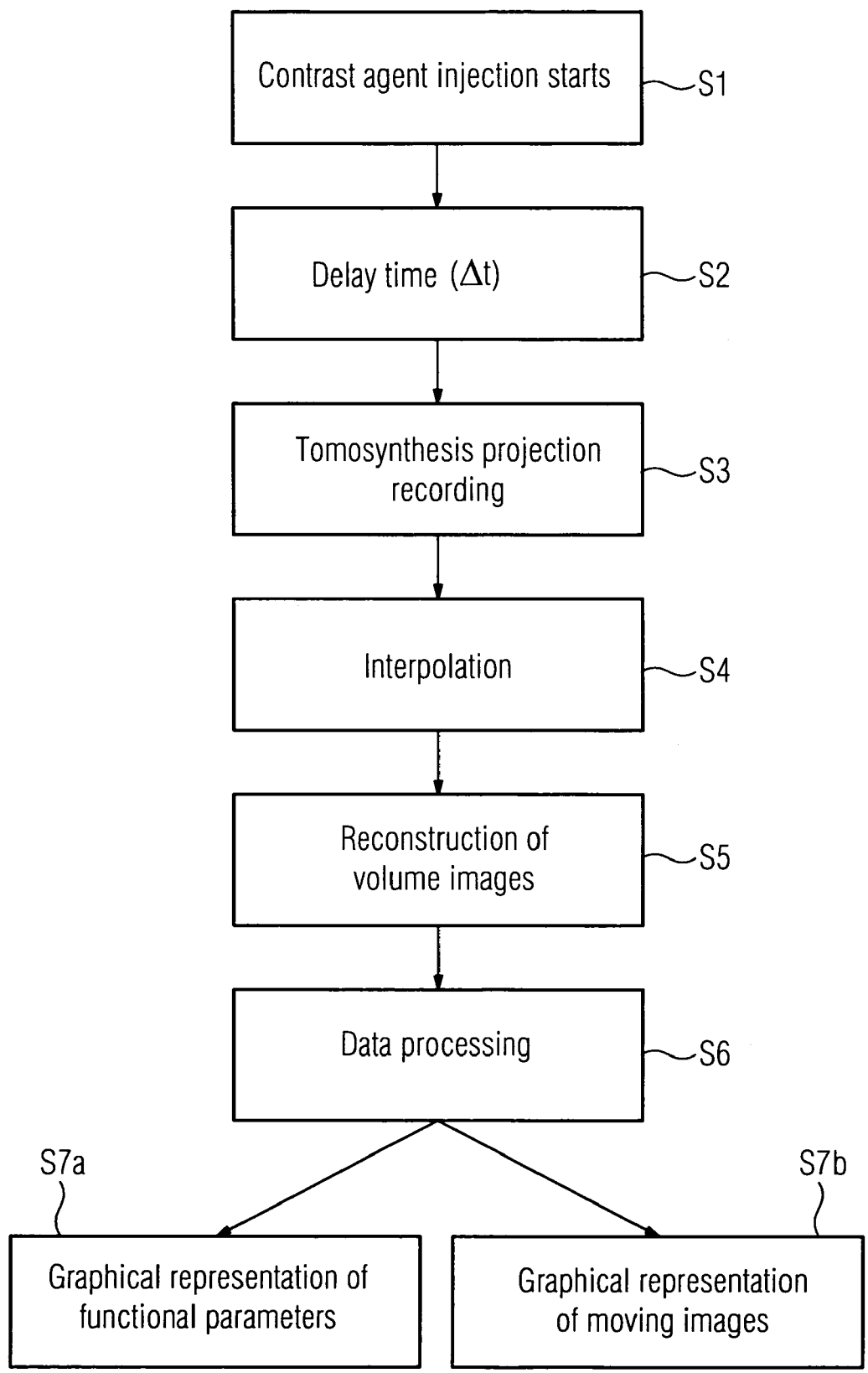
FIG. 12 shows the sequence of operations of the method according to the invention.

The process sequences according to the invention are described below and summarized in the following steps in FIG. 12:

S1 Contrast agent injection starts at the time $t_i$,
S2 Delay time Δt,
S3 Generation of a periodic tomosynthesis projection recording,
S4 Interpolation of tomosynthesis projection recordings at fixed times $t_n$ from the measured data,
S5 Reconstruction of three-dimensional volume images at the times $t_n$, and
S6 Processing and display of data for the user by:
S7a Derivation of functional parameters and graphical display (as is usual in perfusion CT) and/or
S7b Graphical display of moving images (for example for cardiac imaging).

The delay time Δt from the initial injection of contrast agent until the first rotational run is determined from the time of the initial appearance of the contrast agent in the region of interest (ROI).

Interpolation can be effected by means of various algorithms. Here, linear interpolation, polynomial interpolation and spline interpolation can be cited as examples of interpolation algorithms. In principle, however, the use of other interpolation or estimation algorithms is also possible.

Back-projection methods as well as algebraic methods are to be considered for the reconstruction of the volume data, as described in Härer et al. [3], for example.

The representation of the volume data at the times $t_n$ can be effected directly in the form of an animated representation, for example as a "movie" in dynamic angiographical recordings. Alternatively, the reconstructed data can be compressed into functional images or parameters, as employed for example in perfusion measurements such as cerebral blood flow, cerebral blood volume, time-to-peak, etc.

In order to improve the time resolution, the following has been proposed according to the invention:

1. To use tomosynthesis instead of computed tomography to facilitate faster measurement through the use of a smaller scanning range.

2. To use special tomosynthesis scanning paths, which minimize the necessary measurement time and at the same time can be technically optimized, in particular with robot-based C-arm systems.

3. To use suitable time interpolations in order to determine and reconstruct projection images at fixed times $t_0$ from the obtained projections P(s,t).

In principle, tomosynthesis offers the possibility of a faster measurement since in comparison with CT its scanning can be incomplete. It is no longer necessary to record the object under examination from all directions; reconstruction can be effected from a limited scan range, as described in Härer et al. [3], Lauritsch et al. [4] or Badea et al. [5], for example. This offers the potential to carry out the measurement more rapidly. A simple example of this is the use of a partial rotation of the measurement system around the patient instead of using a full CT rotation. However, the choice of scanning path is not limited to the circular rotation of CT. The incompleteness of the data acquisition does in fact limit the image quality—basically the resolution of the image is impaired in a specific direction—but this disadvantage can usually be accepted.

The time-saving of tomosynthesis can essentially be optimized by the use of tomosynthesis scanning paths, which can be cyclically traversed as fast as possible by the measurement system. We propose the use of scanning paths in which the scanning system carries out as few mechanical braking or acceleration operations as possible during the measurement, that is to say the kinetic energy of the measurement system remains as constant as possible. It is particularly advantageous if such paths are realized with a robot-based C-arm system, as described in DE 199 58 864 A1 [6].

Figure 6:
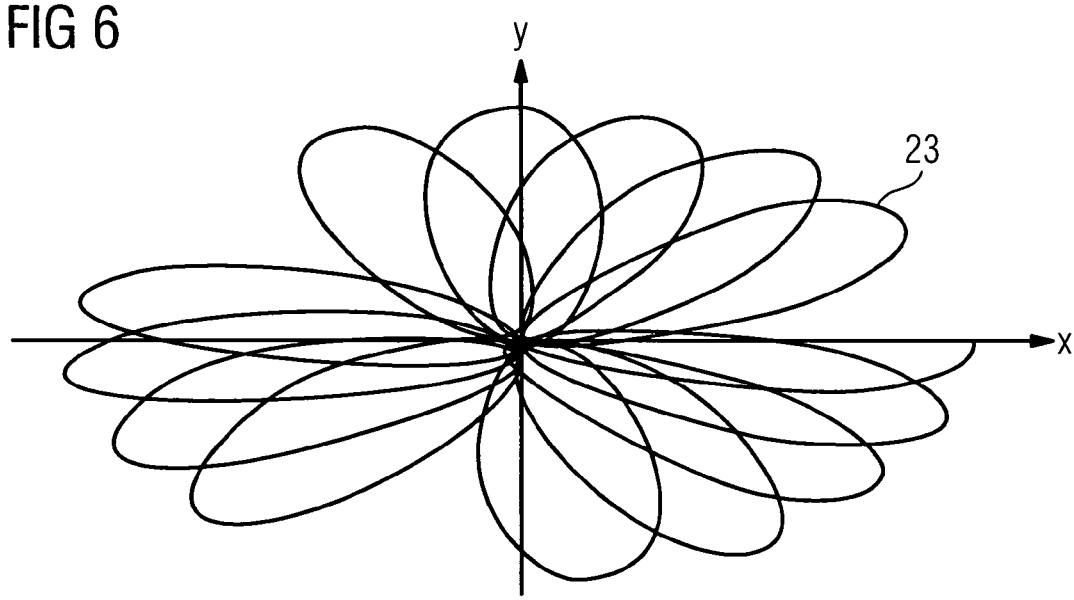

Examples of such advantageous paths are the movement of the focus 11 of the X-ray source 3 and the X-ray image detector 4 on a circle 14, as in FIG. 2, circular tomosynthesis, an ellipse 20 or 21 as in FIGS. 3 and 4, a loop-shaped path 22 or 23 as in FIGS. 5 and 6 or a spiral 24 or 27 as in FIG. 7. The X-ray image detector 4 must register the region of the object being imaged in all projections. At the same time, it can basically move along path shapes other than the focus 11 of the X-ray source 3. Its coupled motion is only necessary in order to keep its area small and thus its costs as low as possible. If the X-ray image detector 4 is large enough to record the region of the object being imaged from all directions, its coupled motion can also be dispensed with. Particularly advantageous are paths in which the kinetic energy remains constant, that is to say the following relationship holds true:

$$E_{kin} = \frac{1}{2}m \cdot \vec{v}^2 = \frac{1}{2}m(\dot{r}^2 + r^2\dot{\varphi}^2) = \text{const.}$$

Forms of movement without the stated additional advantages are, for eV(ample, the linear to-and-fro movement of the scanning system of FIG. 8, linear tomosynthesis or a CT partial rotation, as described in Badea et al. [5], since they require continuous braking or acceleration operations of the measurement system for their periodic performance.

A considerable increase in the time resolution of the reconstruction is achieved by speeding up the scanning through the use of tomosynthesis instead of computed tomography, especially when using scanning paths which can be periodically and speedily traversed. In order to convert the measured data as accurately as possible into volume data, tomosynthesis is combined with an appropriate interpolation or estimation method.

The method according to the invention is therefore based on the combination of a suitable tomosynthesis scanning path—in conjunction with the necessary recording system—a suitable interpolation algorithm and a tomosynthesis reconstruction method.

Within the scope of the invention, floor-mounted and/or ceiling-mounted supports to which the C-arms 2 are attached, can be used instead of the stand 1 as described. The C-arm 2 can also be replaced by a so-called electronic C-arm 2 in which an electronic coupling is established between X-ray emitter 3 and X-ray image detector 4.

However, the C-arms 2 can also be guided on robot arms which are ceiling-mounted or floor-mounted. The method can also be implemented with X-ray apparatus in which each of the individual image-generating components 3 and 4 is supported on a robot arm which is mounted on the ceiling and/or floor.

LITERATURE

[1] M. Zellerhoff, B. Scholz, E.-P. Rührnschopf, T. Brunner, Low contrast 3D-reconstruction from C-arm data, Medical Imaging 2005: Physics of Medical Imaging, Proceedings of SPIE Vol. 5745, pp. 646-655

[2] Günter Lauritsch, Jan Boese, Lars Wigström, Herbert Kemeth and Rebecca Fahrig, Towards Cardiac C-Arm Computed Tomography, IEEE Trans. Med. Imaging 25(7): 922-934 (2006)

[3] Wolfgang H. Härer, Günter Lauritsch and Thomas Mertelmeier, Tomography—Prinzip und Potential der Schichtbildverfahren [Principle and potential of the layer image method], in Th. Schmidt (Pub.), Handbuch diagnostische Radiologie [Manual of Diagnostic Radiology], Vol. 1, Chapter 2.4, Springer Verlag, Berlin, Heidelberg, 2003- ISBN 3-540-41419-32.4

[4] Günter Lauritsch and Wolfgang H. Härer, A theoretical framework for filtered back-projection in tomosynthesis. In: Hanson K M (Hrsg) Medical Imaging 1998: Image Processing Vol. 3338. SPIE, Bellingham (USA), S 1127-1137

[5] C. Badea, Z. Kollitsi, N. Pallikarakis, Image quality in EV(tended arc Filtered Digital Tomosynthesis, Acta Radiologica, Vol. 42, issue 2 (2001);244-249;

[6] DE 199 58 864 A1: Röntgeneinrichtung mit einem Roboterarm zur Positionierung einer Röntgenquelle und eines Röntgendetektors [X-ray apparatus with a robot arm for positioning an X-ray source and an X-ray detector].

The invention claimed is:

1. A method for generating a tomosynthesis volume image of an object by a tomographic method, comprising:
   recording a plurality of tomosynthesis projection recordings of the object along a tomosynthesis scanning path;
   interpolating the tomosynthesis projections recordings using an interpolation algorithm for generating a projection data set;
   generating a tomosynthesis volume image using a tomosynthesis reconstruction method based on the projection data set;
   injecting a contrast agent;
   waiting for a delay time;
   recording tomosynthesis projections periodically;
   interpolating the periodic tomosynthesis projection recordings at a fixed time;
   generating a tomosynthesis volume image at the fixed time; and
   displaying the tomosynthesis volume images.

2. The method as claimed in claim 1, wherein the tomosynthesis scanning path is a closed path.

3. The method as claimed in claim 1, wherein the tomosynthesis scanning path is selected from the group consisting of: a circular path, an elliptical path, a looped path, and a spiral path.

4. The method as claimed in claim 1, wherein the tomosynthesis scanning path is a non-closed path.

5. The method as claimed in claim 4, wherein the tomosynthesis scanning path is a spiral path or a linear path.

6. The method as claimed in claim 5, wherein the tomosynthesis scanning path is traversed in both directions.

7. The method as claimed in claim 1, wherein the interpolation algorithm is selected from the group consisting of: a nearest neighbor interpolation, a linear interpolation, a polynomial interpolation, and a spline interpolation.

8. The method as claimed in claim 1, wherein the tomosynthesis reconstruction method is a back-projection method or an algebraic method.

9. The method as claimed in claim 1, wherein a tomosynthesis representation of the object is displayed from the tomosynthesis volume image.

10. The method as claimed in claim 9, wherein the display of the tomosynthesis representation comprises an animated representation or a graphical representation of a functional parameter.

11. The method as claimed in claim 10, wherein the animated representation is a dynamic angiographical recording.

12. The method as claimed in claim 10, wherein the graphical representation is a derivation of the functional parameter and a graphical representation of cerebral blood flow, or cerebral blood volume, or time-to-peak.

13. The method as claimed in claim 1, wherein the display of the tomosynthesis volume image comprises a graphical display of moving images.

14. The method as claimed in claim 13, wherein the steps of the interpolating data of the tomosynthesis projection recordings and the generating the tomosynthesis volume image are repeated at all interest times.

15. The method as claimed in claim 1, wherein the tomosynthesis projection recordings are registered at different recording angles between a start position and an end position.

16. The method as claimed in claim 1, wherein the object is a moving structure.

17. A method for generating a tomosynthesis volume image of an object by a tomographic method, comprising:
   recording a plurality of tomosynthesis projection recordings of the object along a tomosynthesis scanning path at a plurality of different recording angles; and
   reconstructing a tomosynthesis volume image from the tomosynthesis projection recordings;
   injecting a contrast agent;
   waiting for a delay time;
   recording tomosynthesis projections periodically;
   interpolating the periodic tomosynthesis projection recordings at a fixed time;
   generating a tomosynthesis volume image at the fixed time; and
   displaying the tomosynthesis volume images.

18. An imaging unit for generating a tomosynthesis volume image of an object by a tomographic method, comprising:
   an V(-ray source;
   an V(-ray image detector that records a plurality of tomosynthesis projection recordings of the object along a tomosynthesis scanning path; and
   an imaging processing unit that:
      interpolates data of the tomosynthesis projection recordings using an interpolation algorithm for generating a projection data set,
      generates a tomosynthesis volume image using a tomosynthesis reconstruction method based on the projection data set,
      injects a contrast agent,
      waits for a delay time,
      records tomosynthesis projections periodically,
      interpolates the periodic tomosynthesis projection recordings at a fixed time,
      generates a tomosynthesis volume image at the fixed time, and
      displays the tomosynthesis volume images.

\* \* \* \* \*